United States Patent
Nino et al.

(10) Patent No.: US 10,688,634 B2
(45) Date of Patent: Jun. 23, 2020

(54) GEARLESS SPRING WASHER HIGH TORQUE DEVICE

(71) Applicant: ECA Medical Instruments, Newbury Park, CA (US)

(72) Inventors: John Nino, Simi Valley, CA (US); David Ivinson, Camarillo, CA (US); David Tory, Camarillo, CA (US)

(73) Assignee: ECA Medical Instruments, Newbury Park, CA (US)

( * ) Notice: Subject to any disclaimer, the term of this patent is extended or adjusted under 35 U.S.C. 154(b) by 372 days.

(21) Appl. No.: 15/583,803

(22) Filed: May 1, 2017

(65) Prior Publication Data

US 2017/0232592 A1    Aug. 17, 2017

Related U.S. Application Data

(63) Continuation of application No. PCT/US2016/055798, filed on Oct. 6, 2016, and a
(Continued)

(51) Int. Cl.
*B25B 23/157* (2006.01)
*B25B 23/14* (2006.01)
(Continued)

(52) U.S. Cl.
CPC ........ *B25B 23/141* (2013.01); *A61B 17/8875* (2013.01); *B25B 23/0035* (2013.01);
(Continued)

(58) Field of Classification Search
USPC .............................. 81/52, 472, 474, 475, 476
See application file for complete search history.

(56) References Cited

U.S. PATENT DOCUMENTS

| 3,695,059 A | 10/1972 | Laubach |
| 5,180,042 A | 1/1993 | Ogiso |

(Continued)

FOREIGN PATENT DOCUMENTS

| DE | 2427352 A1 | 12/1975 |
| EP | 1110512 A1 | 6/2001 |
| WO | WO 2014/116414 A1 | 7/2014 |

OTHER PUBLICATIONS

International Patent Application No. PCT/US2016/55798; Int'l Written Opinion and Search Report; dated Dec. 29, 2016; 8 pages.
(Continued)

*Primary Examiner* — Joseph J Hail
*Assistant Examiner* — Shantese L McDonald
(74) *Attorney, Agent, or Firm* — Ferguson Case Orr Paterson

(57) ABSTRACT

Disposable torque-limiting mechanisms with upper shank component with a torque-limiting interface, a lower shank component with a torque-limiting interface, and a washer assembly biasing element. Torque-limiting interfaces having a plurality of undulations arranged around an axial bore or drive socket and separated by a plurality of transition regions, with each undulation having an upslope, a peak, and a downslope. The torque-limiting interfaces are configured to engage and disengage to provide torque transmission with predetermined torque limits at various rotational speeds and for amounts of actuations while remaining within a specified operational range.

23 Claims, 11 Drawing Sheets

Related U.S. Application Data continuation of application No. PCT/US2016/035712, filed on Jun. 3, 2016.

(60) Provisional application No. 62/238,359, filed on Oct. 7, 2015, provisional application No. 62/238,419, filed on Oct. 7, 2015, provisional application No. 62/345,607, filed on Jun. 3, 2016.

(51) Int. Cl.
    *B25B 23/00*      (2006.01)
    *F16D 7/04*      (2006.01)
    *B25B 23/147*      (2006.01)
    *A61B 17/88*      (2006.01)
    *A61B 90/00*      (2016.01)

(52) U.S. Cl.
    CPC ............ *B25B 23/147* (2013.01); *F16D 7/044* (2013.01); *A61B 2090/031* (2016.02)

(56) References Cited

U.S. PATENT DOCUMENTS

| | | |
|---|---|---|
| 6,487,943 B1 | 12/2002 | Jansson et al. |
| 7,938,046 B2 | 5/2011 | Nino et al. |
| 8,365,641 B2 | 2/2013 | Daglow |
| 9,241,751 B2 | 1/2016 | Nino et al. |
| 10,131,040 B2 | 11/2018 | Nino et al. |
| 2006/0016300 A1 | 1/2006 | Bubel |
| 2007/0289391 A1* | 12/2007 | Gao ................ B25B 23/141 73/862.21 |
| 2012/0055296 A1* | 3/2012 | Landowski ........ B25B 23/1427 81/474 |
| 2013/0305889 A1* | 11/2013 | Nino .................. B25B 15/04 81/475 |
| 2014/0000420 A1 | 1/2014 | Chuang |
| 2015/0151416 A1 | 6/2015 | Chen |
| 2016/0184043 A1 | 6/2016 | Ivinson et al. |
| 2017/0232592 A1 | 8/2017 | Nino et al. |
| 2018/0223912 A1 | 8/2018 | Nino et al. |
| 2018/0290274 A1 | 10/2018 | Nino et al. |

OTHER PUBLICATIONS

International Patent Application No. PCT/US2016/035712; Int'l Written Opinion and Search Report; dated Sep. 12, 2016; 13 pages.
International Patent Application No. PCT/US2016/055798; Int'l Preliminary Report on Patentability; dated Apr. 19, 2018; 8 pages.
"Sinusoidal clutch gives screwdriver precise torque"; Project Engineering; vol. 44; Feb. 1973; p. 14-15.
European Patent Application No. 16854340.3; Extended Search Report; dated Mar. 27, 2019; 8 pages.

\* cited by examiner

SECTION F-F

Time [Seconds]

GEARLESS SPRING WASHER HIGH TORQUE DEVICE

CROSS-REFERENCE TO RELATED APPLICATIONS

This application is a Continuation Patent Application of International Patent Application PCT/US2016/055798, filed Oct. 6, 2016, claiming priority to U.S. Provisional Patent Application 62/238,419, filed Oct. 7, 2015, U.S. Provisional Patent Application 62/238,359, filed Oct. 7, 2015, U.S. Provisional Patent Application 62/345,607, filed Jun. 3, 2016, and International Patent Application PCT/US2016/035712, filed Jun. 3, 2016, the contents of which are incorporated here in their entirety.

BACKGROUND

1. Field

This disclosure relates to gearless torque drives for torque-limiting devices that are suitable for operation at high rotational speeds.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Power tools are used for some applications in the medical industry. Such power tools can provide torque to a workpiece while also providing higher rotational rates than can be provided with manually driven tools. Torque-limiting systems can be utilized with medical power tools, either as an additional attachment provided in-line between the power tool and the workpiece or as internalized systems within the power tool itself. Reusable torque-limiting systems need to be sterilized between uses and typically must be serviced and recalibrated periodically to ensure performance within specifications. Disposable torque-limiting systems are an alternative to the reusable systems. Once the torque-limiting system has been used, it is discarded.

Disposable torque-limiting devices which are inexpensive for use with power tools can fall out of specification with increased RPMs and as such fail to perform sufficiently.

Thus there is a need for disposable torque-limiting systems that can be utilized with medical power tools to limit applied torque at higher rotational speeds and remain in specification over a predetermined number of actuations. The disclosure is directed to these and other important needs.

DISCLOSURE

Aspects of exemplars of torque-limiting devices, methods and mechanisms are disclosed herein, in some exemplars a generally hollow cylindrical body with a partially closed distal end provides an upper shank formed inside the partially closed distal end of the cylindrical body; a circumferential rim is formed on the outside of the partially closed dial end; an upper torque-limiting interface is formed on the inside of the partially closed distal end having an axial bore; a lower shank component is placed in the body and free to rotate axially, it further comprises a proximal end, a distal end, a neck extending from the distal end, a drive socket fluidly connecting the proximal end and the distal end, and a lower torque-limiting interface disposed on the proximal end, wherein the upper shank component and the lower shank component are aligned along an axis in the direction of the axial bore and the drive socket with the first torque-limiting interface in contact with the second torque-limiting interface; an MBWA placed above the lower shank on at least partially around the neck configured to apply compressive force (F) along the axis to compress the first torque-limiting interface against the second torque-limiting interface; a tool collar with a flange extending radially therefrom with a front on one side of the flange, a square leg formed on the opposite of the flange and a shaped channel therethrough is rotatably fit into the circumferential rim; a tool shaft with a threaded back portion and a front end having a tool channel therein; catches are formed on the tool shaft configured to mate with the shaped channel whereby the tool shaft can be inserted through the tool collar but rotate within the shaped channel; a threaded retaining member is configured to engage the threaded back portion; and wherein the tool shaft and threaded retaining member cooperate to apply a predetermined force to the lower and upper shanks, (the two interfaces together form a torque limiting engagement), by mounted the tool shaft through the tool collar, the axial bore, the drive socket and the MBWA and affixing the retaining member thereto.

In some instances in the above exemplars the MBWA is configured to apply compressive force (F) along the axis to compress the first torque-limiting interface against the second torque-limiting interface; the upper shank component and the lower shank component are configured to engage to rotate together when torque is applied to the lower shank component via the drive socket; and, the upper shank component and the lower shank component are configured to disengage when a predetermined torque limit is exceeded.

In some instances the above exemplars further comprise a plastic high lubricity washer between the flange and the circumferential rim. In yet other instances the exemplars include a roller bearing washer between the flange and the circumferential rim.

Disclosed is a novel disposable torque-limiting device with one or more of a torque limiting interface, a drive assembly with reduced components, a shaped washer force assembly with reduced components, simple assembly, operation for a limited predetermined number of cycles at high speed. Cycles are a measure of the life time of the disposable device.

Aspects of exemplars of torque-limiting devices, methods, and mechanisms are disclosed herein, in some exemplars a generally hollow cylindrical body with a partially closed distal end provides an upper shank formed inside the partially closed distal end of the cylindrical body; a circumferential rim is formed on the outside of the partially closed dial end; an upper torque-limiting interface is formed on the inside of the partially closed distal end having a axial bore; a lower shank component having a proximal end, a distal end, a retaining cavity formed thereon, a drive socket fluidly connecting the proximal end and the distal end, and a lower torque-limiting interface disposed on the proximal end, wherein the upper shank component and the lower shank component are aligned along an axis in the direction of the axial bore and the drive socket with the first torque-limiting interface in contact with the second torque-limiting interface; an MBWA placed above the lower shank on at least partially around the neck configured to apply compressive force (F) along the axis to compress the first torque-limiting interface against the second torque-limiting interface; a tool collar with a flange extending radially therefrom with a front on one side of the flange, a square leg formed on the opposite of the flange and a shaped channel therethrough is rotatably fit into the circumferential rim; a tool shaft with a threaded back portion and a front end having a tool channel therein; catches are formed on the tool shaft configured to mate with the shaped channel whereby the tool shaft can be inserted through the tool collar but rotate within the shaped channel; a threaded retaining member is configured to engage the threaded back portion; and wherein the tool shaft and threaded retaining member cooperate to apply a predetermined force to the lower and upper shanks, (and the two interfaces together form a torque limiting engagement), by mounted the tool shaft through the tool collar, the axial bore, the drive socket and the MBWA and affixing the retaining member thereto.

In some instances in the above exemplars the MBWA is configured to apply compressive force (F) along the axis to compress the first torque-limiting interface against the second torque-limiting interface; the upper shank component and the lower shank component are configured to engage to rotate together when torque is applied to the lower shank component via the drive socket; and, the upper shank component and the lower shank component are configured to disengage when a predetermined torque limit is exceeded.

In some instances the above exemplars further comprise a plastic high lubricity washer between the flange and the circumferential rim. In yet other instances the exemplars include a roller bearing washer between the flange and the circumferential rim. In some instances the above exemplars further comprise a tool in the tool channel.

In some instances in the above exemplars the first torque-limiting interface has a first plurality of undulations arranged around the axial bore and separated by a first plurality of transition regions; the second torque-limiting interface comprises a second plurality of undulations arranged around the drive socket and separated by a second plurality of transition regions, the first and second pluralities being equal in number; and each undulation comprises an upslope, a peak, and a downslope.

In some instances in the above exemplars of the torque-limiting device each upslope has an inclination angle between about 3 degrees and about 15 degrees.

In some instances in the above exemplars of the torque-limiting device each upslope has an inclination angle between about 5 degrees and about 9 degrees.

In some instances in the above exemplars of the torque-limiting device each upslope has an inclination angle between about 6 degrees and about 8 degrees.

In some instances in the above the predetermined torque limit is between about 0.1 Newton-meters and 3.0 Newton-meters. In some instances in the above exemplars the predetermined torque limit is between about 3.0 Newton-meters and 6.0 Newton-meters.

In some instances in the above exemplars of the torque-limiting device the first torque-limiting interface and second torque-limiting interface each comprise between two and five undulations. In some instances in the above exemplars of the torque-limiting device the first torque-limiting interface and second torque-limiting interface each comprise three undulations.

In some instances in the above exemplars of the torque-limiting device the disposable torque limiting device is a generally hollow cylindrical body with a partially closed distal end; an upper shank formed inside the partially closed distal end of the cylindrical body; a circumferential rim formed on the outside of the partially closed dial end; an upper torque-limiting interface having undulations formed on the inside of the partially closed distal end having a axial bore; a lower shank component rotatable placed within the cylindrical body comprising a proximal end, a distal end, a retaining cavity formed thereon, a drive socket fluidly connecting the proximal end and the distal end, and a lower torque-limiting interface having undulations disposed on the proximal end, wherein the upper shank component and the lower shank component are aligned along an axis in the direction of the axial bore and the drive socket with the first torque-limiting interface in contact with the second torque-limiting interface; an MBWA placed above the lower shank inside the retaining cavity configured to apply compressive force (F) along the axis to compress the first torque-limiting interface against the second torque-limiting interface at a predetermined torque limit; a tool collar with a flange extending radially, a front on one side of the flange, a square leg formed on the opposite of the flange and a shaped channel there through rotatably fit into the circumferential rim; a tool shaft with a threaded back portion and a front end having a tool channel therein; catches formed on the tool shaft configured to mate with the shaped channel whereby the tool shaft can be inserted through the tool collar but rotate within the shaped channel; and a threaded retaining member configure to engage the threaded back portion.

In some instances each undulation is a complex shaped wave which limits degradation of inexpensive plastic materials and provides nominal torque.

In some instances the first section of each undulation with a higher shoulder near the center of the shank and a slope downward to the perimeter of the shank; a second section having a wide plateau; a third section having a plateau wider than the second section; a fourth section having a plateau with height greater than all other section; and a fifth section forming a sloped transition region.

In some instances in the above exemplars of the torque-limiting device the torque-limiting mechanism provides a predetermined torque between about 0.1 Newton-meter and about 6.0 Newton-meters of torque at a rotational speed between about 50 RPM and about 1300 RPM over at least one of 5, 10, 20, 30, 40, 50, 60, 70, 80, 90, 100, 105, 110, 120, 150, 180, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, or 2500 actuations while remaining within a specified operational range.

DRAWINGS

The above-mentioned features of the present disclosure will become more apparent with reference to the following description taken in conjunction with the accompanying drawings wherein like reference numerals denote like elements. In addition, the drawings are not necessarily drawn to scale. In the drawings.

Figure 7A:
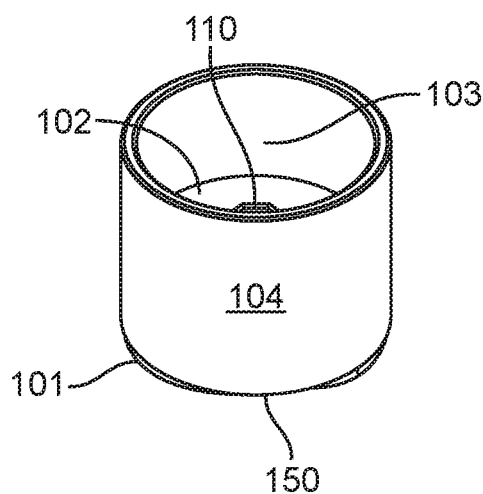
Figure 7B:
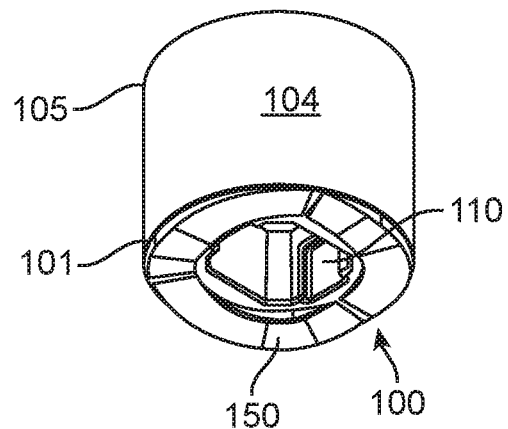
Figure 7C:
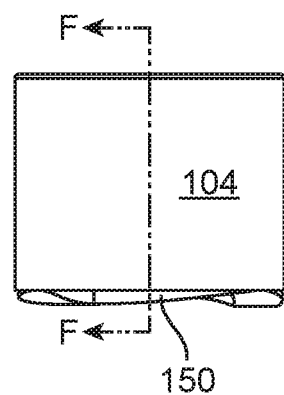
Figure 7D:
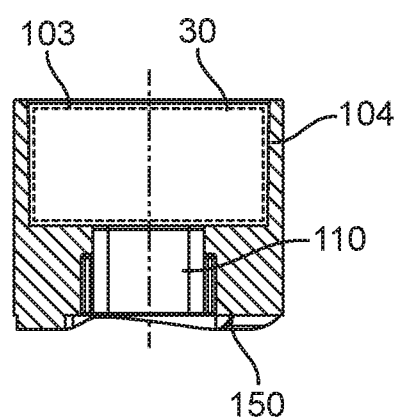

FIGS. 7A and 7B show perspective views of some aspects of components of torque-limiting mechanisms of the present disclosure. FIG. 7C shows a side view of some aspects of components of torque-limiting mechanisms of the present disclosure. The distal end 102 of the lower shank is visible. The open top 105 of the annular wall forming retaining cavity 103 is also visible. FIG. 7D shows a cut-away section view along the section marked F-F in FIG. 7C.

Figure 8A:
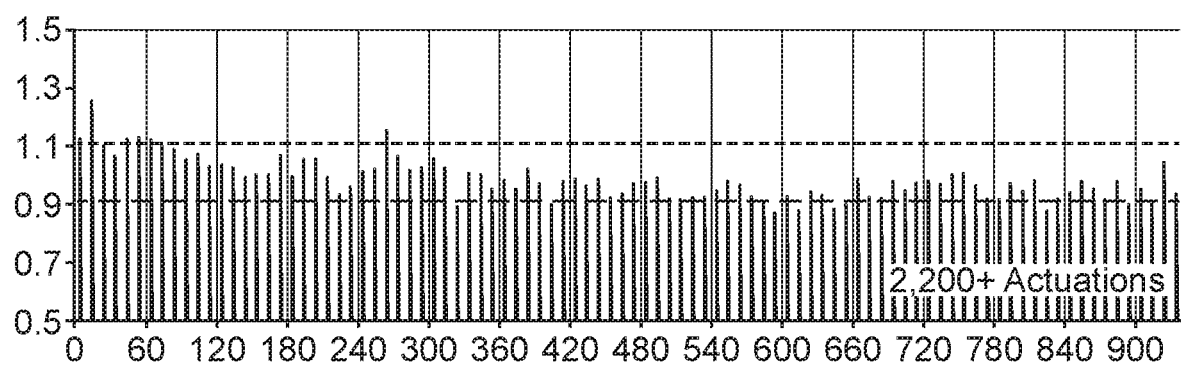
Figure 8B:
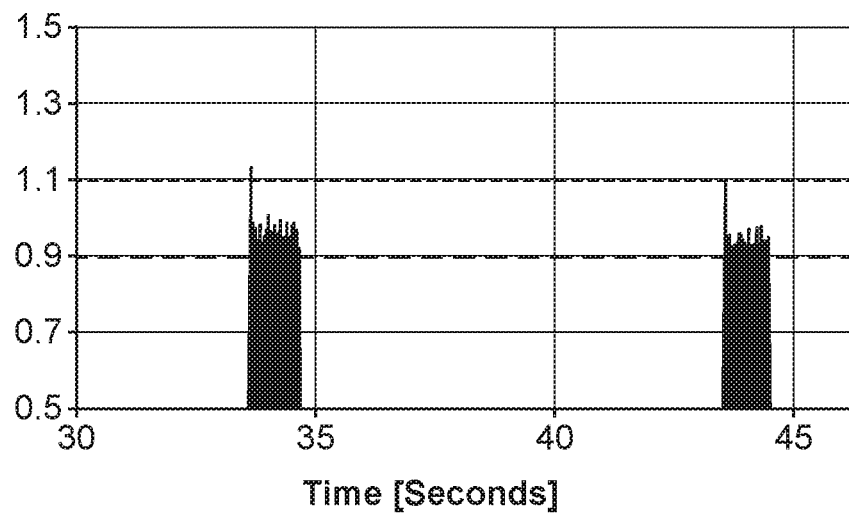

FIGS. 8A and 8B show testing data from testing of an implementation of the torque-limiting mechanisms of the present disclosure.

Figure 8C:
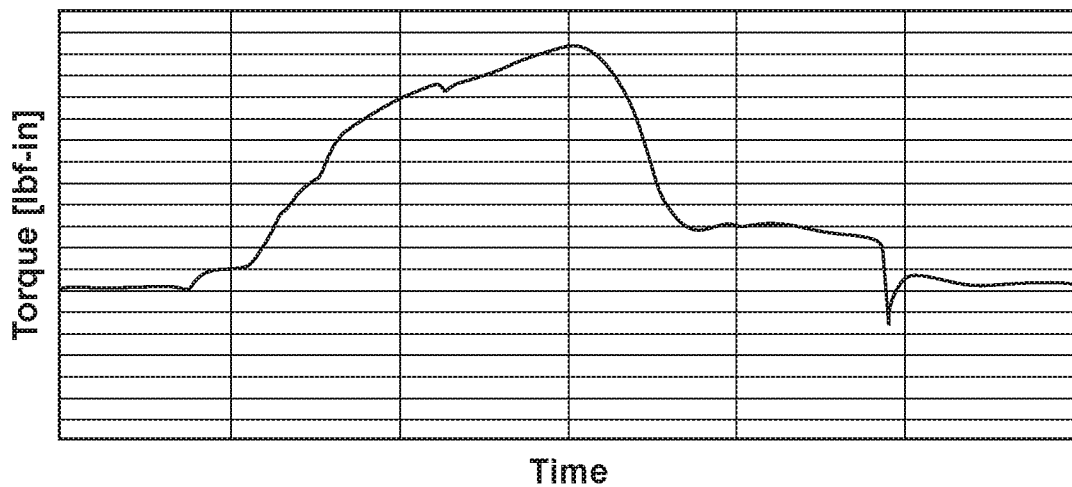

FIG. 8C shows testing data from testing of a prior art torque-limiting mechanism.

Figure 8D:
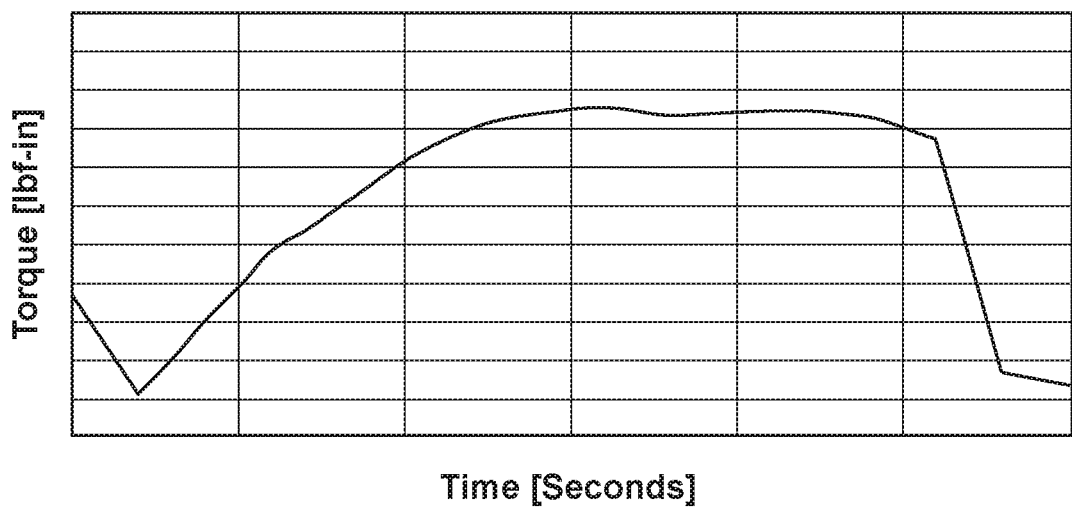

FIG. 8D shows testing data from testing of an implementation of the torque-limiting mechanisms of the present disclosure.

As shall be appreciated by those having ordinary skill in the art, the figures are not to scale, and modifications to scale within a figure or across the figures are considered within the present disclosure. All callouts in Figures are hereby incorporated by this reference as if fully set forth herein.

FURTHER DISCLOSURE

Aspects of torque-limiting drivers are provided in exemplary implementations of this disclosure. Those of ordinary skill in the art will recognize small design variations that are within the scope of this disclosure. The identification of some aspects and not others shall not be considered limiting in the disclosure but may be limitations in claims.

FIGS. 1A-1E illustrate aspects of implementations of torque-limiting in-line drivers 10. FIGS. 2-7D illustrate additional aspects of torque limiting drivers including operation of the torque limiter.

The driver has a generally cylindrical shape with a cup shaped drive cap 12 with connector mount or other structure to facilitate use by a user. In some instances the drive cap may support or be connected to a handle or other finger fold to allow manual rotation of the device. For example, the drive cap is affixed to a generally hollow cylindrical body 14. The cap 12 is mated to the cylindrical body at the proximal end 15 of the cylindrical body. The cap 12 may be snap-fitted to cylindrical body 14, or may be welded, adhered, or attached by any equivalent thereof.

The hollow cylindrical body 14 has an open distal end 16 with a circumferential rim 17 on the exterior therein proving a seat and guide for a tool collar 20. A lower shank 100 is fit inside the body 14. The lower shank is generally cylindrical of a size to allow to rotate axially within the body. Opposite the circumferential rim on the interior 18 of the cylindrical body 14 is an upper shank component 200 formed as part of the cylindrical hollow body 14 with at least an axial bore 210 and a upper or second torque-limiting interface 250 disposed on the inside of the cylindrical body 14.

The tool collar is formed of plastic and is a guide for a shaft. The tool collar 20 has a flange 22 extending radially of a size and shape to fit rotatably into the circumferential rim 17. The tool collar has a roughly square leg 25 extending on one side of the flange 22 and a nose 27 extending on the opposite of the flange. A shaped channel 29 passes through the tool collar thereby forming a fluid connection.

Figure 1A:
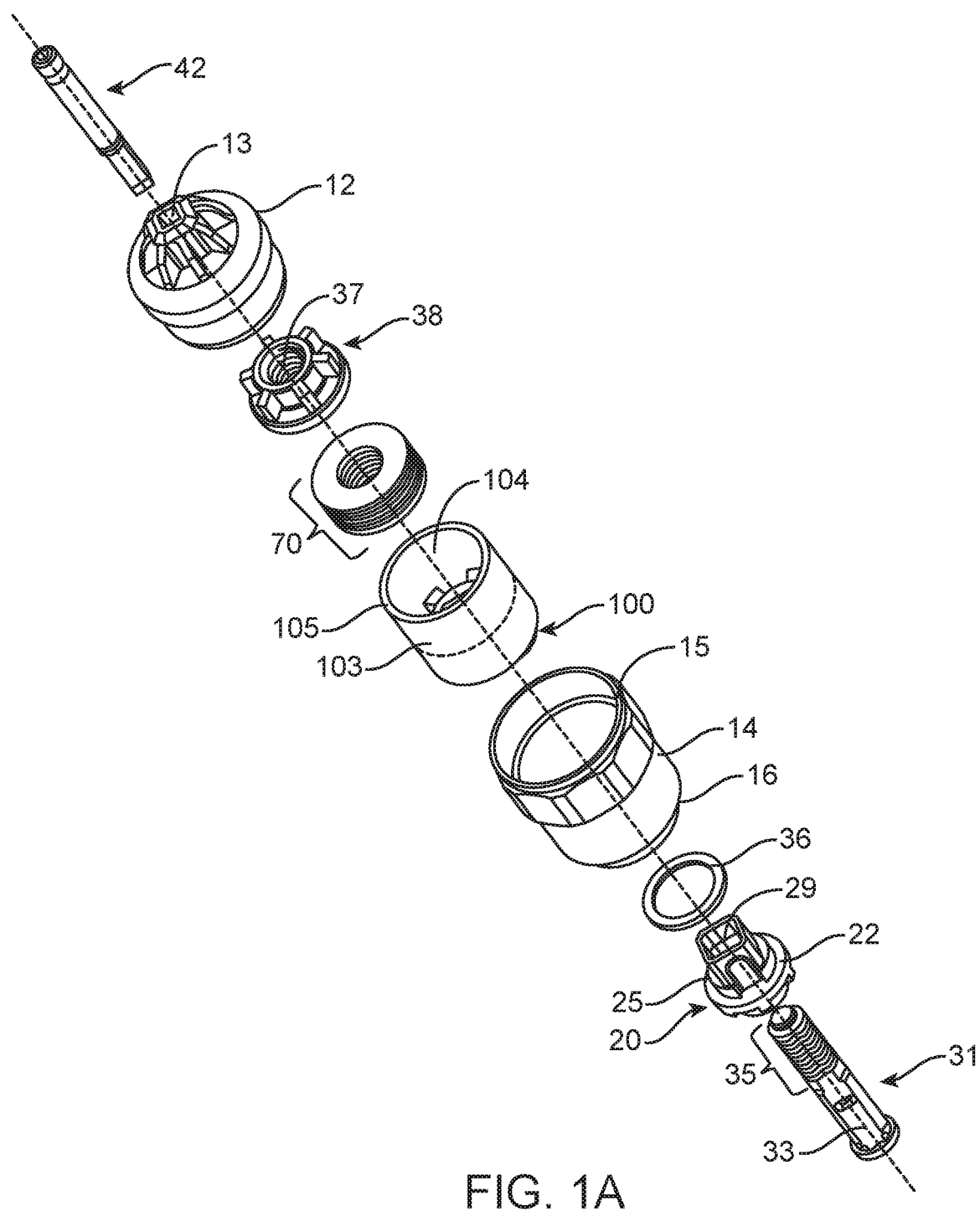
FIG. 1A shows an exploded assembly perspective view back to front of some aspects of an in-line torque limiting device of the present disclosure.
Figure 1B:
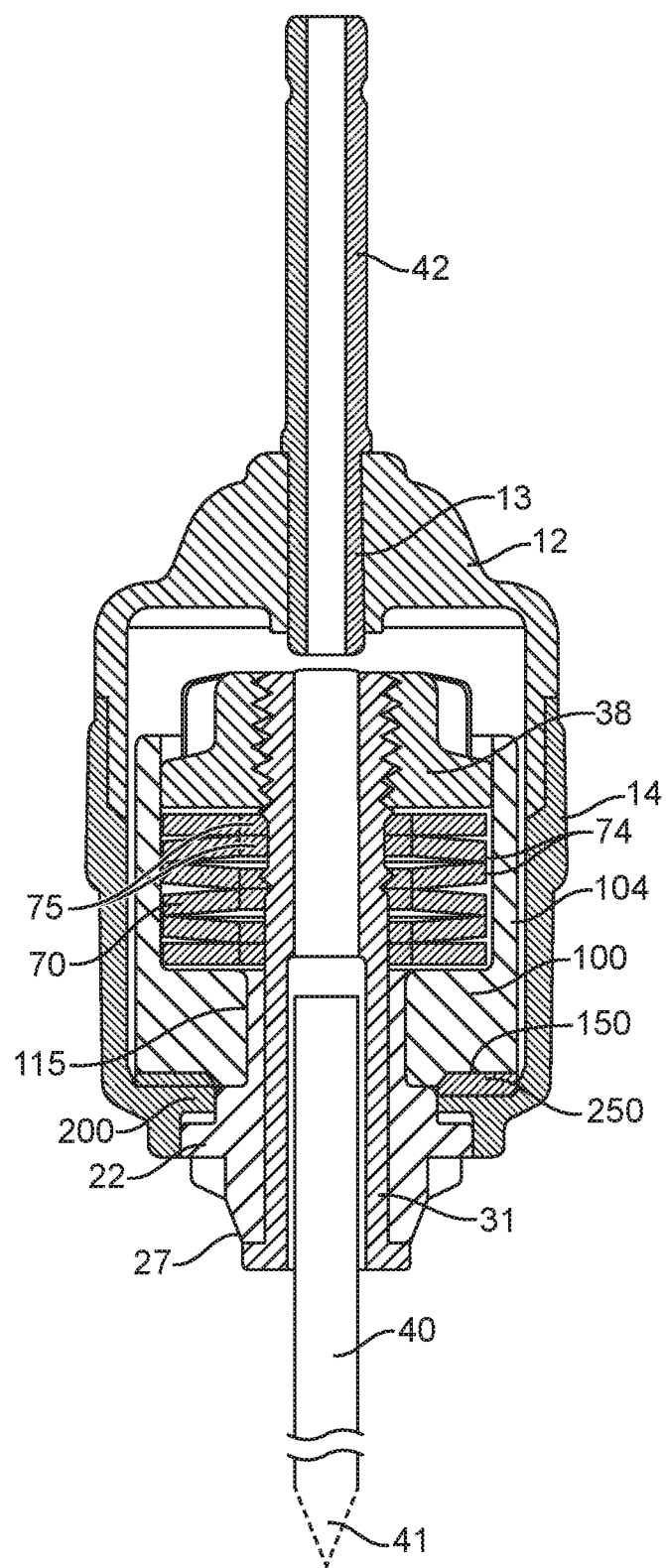
FIG. 1B shows a cutaway front view of some aspects of an in-line torque limiting device of the present disclosure.
Figure 1C:
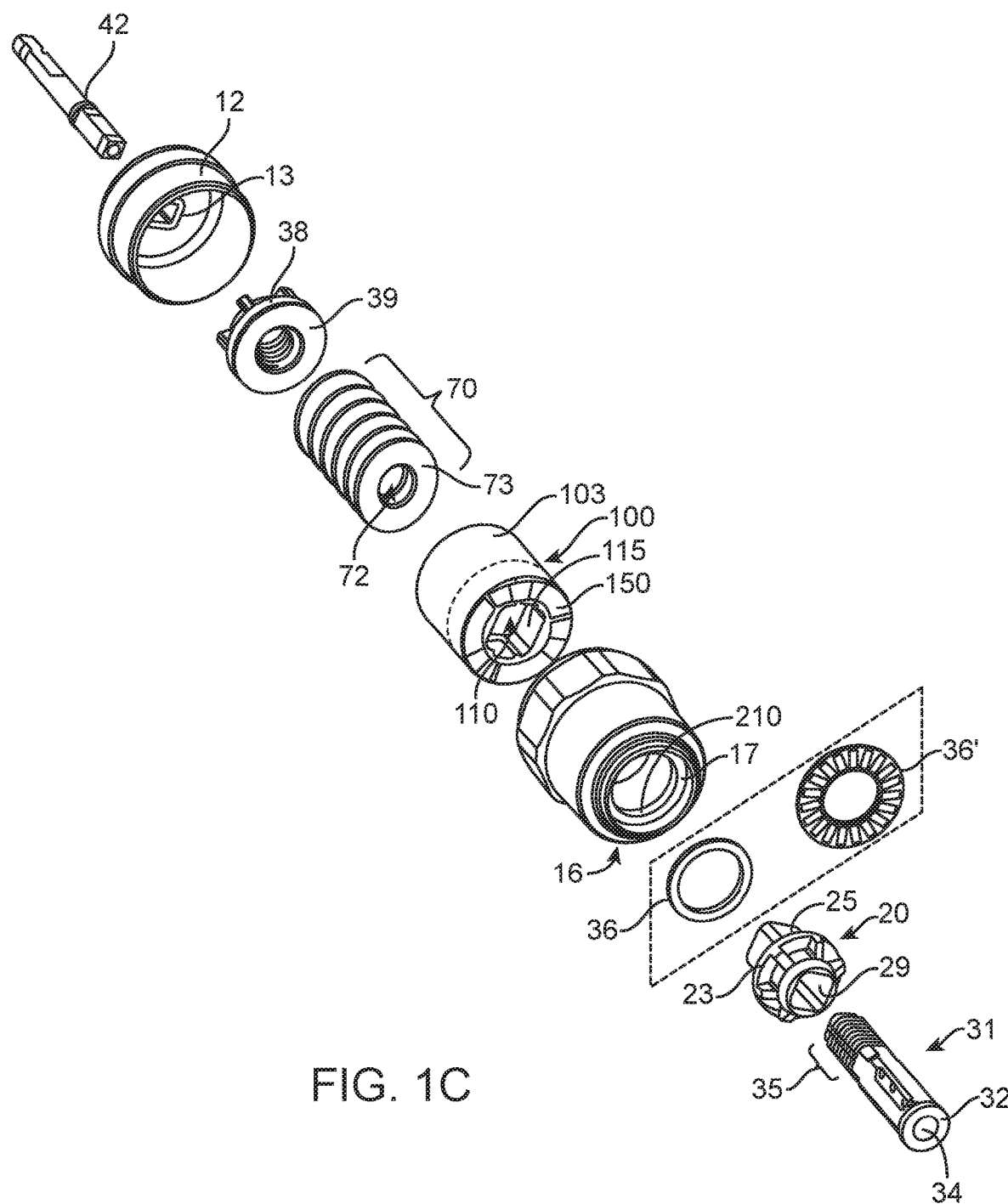
FIG. 1C shows an exploded assembly perspective view front to back of some aspects of an in-line torque limiting device of the present disclosure.
Figure 1D:
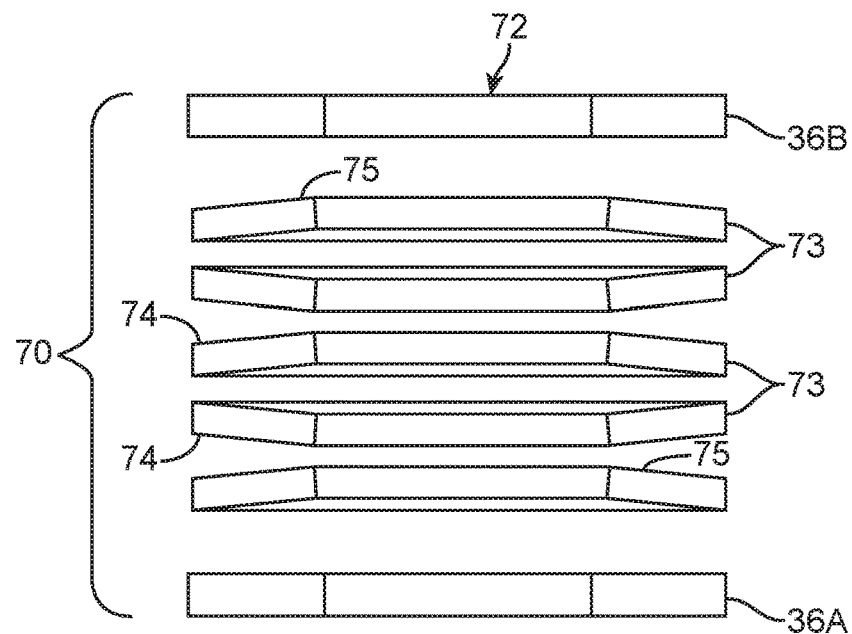
FIGS. 1D and 1E show side views of biasing assembly arrangements.
Figure 1E:
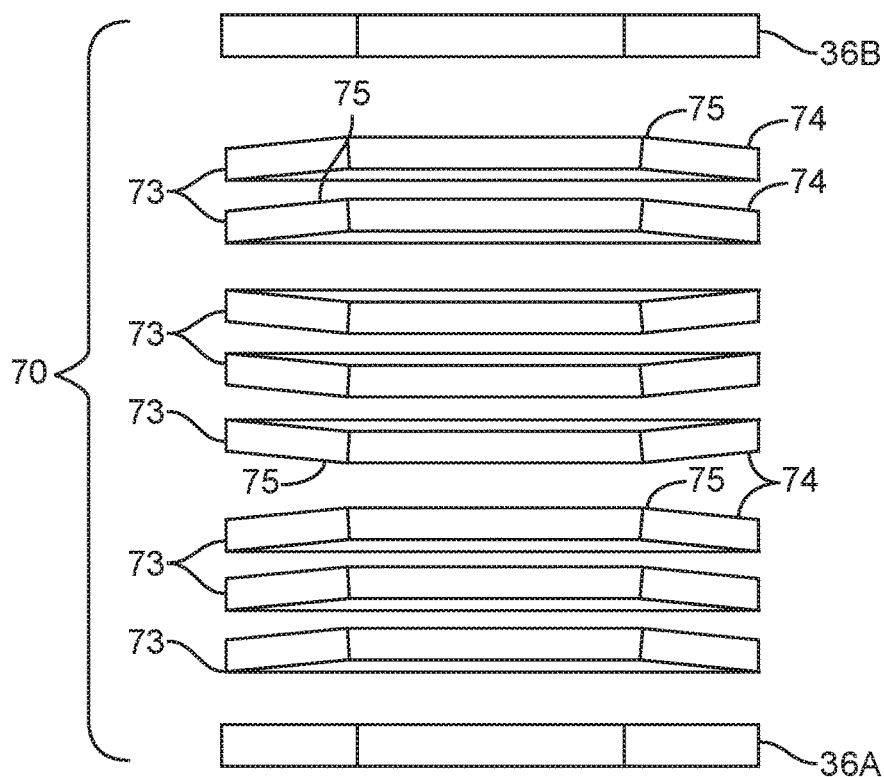

During assembly the lower shank component 100 fits movably within the hollow body 14. The lower shank has a drive shaft 110 therethrough. On one side of the lower shank there is a lower or first torque-limiting interface 150 and the other side of the lower shank 100 may include a retaining cavity 103 configured to retain biasing elements, such as a grouping of belleville washers, also known as a coned-disc spring, hereinafter referred to as Multiple Belleville Washer Assembly ("MBWA") 70 with a fluid passage 72 through the center of member. Each washer member 73 has a base 74 and a cone 75 and they are set in pairs alternating with base 74 to base 74 and cone 75 to cone 75 with a fluid passage 72 therethrough. In other instances the washer members 73 are stacked as shown in FIG. 1E. A flat washer 36A and 36B are placed on either end of the stack of washer members 73. In some implementations, compressible materials with durometer ratings between about 50 durometer and 100 durometer are used, within an annular wall 104. A tool shaft 31 fits firmly into the tool collar channel 29. The tool shaft may be partially hollow with an open front end 31. One or more catches 33 are formed on a portion of the tool shaft whereby the catches mate with the channel 29 and the tool shaft 32 is restricted from rotation within the channel 29. The catches are depicted as one or more flat sides in FIGS.

1A-1C. A tool channel 34 extends axially, at least partially, in the tool shaft from the front end 31 of the tool shaft. A series of threads 35 are formed on a back portion of the tool shaft 32. Optionally a first washer 36 is interposed between the flange and circumferential rim 17. The washer is formed of plastic and has high lubricity. In some instances depending on design requirements and use a flat roller bearing washer 36' between a first washer 36C and a second washer 36D may be used with or in place of the washer 36. At higher speed the roller bearing washer reduces frictional forces at the circumferential rim 17. Aspects of the method of in-line torque application at predetermined forces include reducing or eliminating melting of the circumferential rim during the life time of the device.

The lower shank 100 is inserted into the body 14 through the proximal end 15 and the lower torque-limiting interface 150 sits on the upper torque-limiting interface 250 and the two interfaces together form a torque limiting engagement. The lower shank is generally cylindrical of a size to allow to rotate axially within the body. The square leg and tool shaft extends through the axial bore 210 and the drive shaft 110. Formed as part of the drive shaft 110 are a series of drive catches 115 which mate with the square legs 25 whereby when the lower shank 100 rotates the square leg rotates as does any tools and the affixed therein.

A threaded 37 retaining member 38 such as a nut or other fixture fits onto the threads 35 of the tool shaft and is used to compress the MBWA 70 against the lower shank and hold the components inside the device inline. Optionally, a washer 39 may be placed between the MBWA 70 and retaining member 38. This engagement provides a locking mechanism for tool shaft 32 relative to the body 14 via lower shank 100 when pressure is applied across lower shank 100 and upper shank 200. A preselected force is applied across lower shank 100 and upper shank 200 via MBWA 70 within cylindrical body 14. To seal the device, at the end of the drive cap 12 is the connector mount 13 shown formed on the drive cap. The connector mount 13 provides a fixation of a back drive shaft 42 for a powered in-line torque limited driver (not shown).

In operation the drive shaft 40 which has a workpiece engaging tip 41 is connected via the tip to a workpiece, fastener, or other fixture that requires rotation for application. The application of a rotational force to the device causes the first torque-limiting interface 150 and the second torque-limiting interface 250 (collectively referred to as the torque limiter) support on the shanks to engage and rotate the tool until such time as the amount of force necessary to rotate the tool further is exceeded by the force the tool is experiencing during operation. At that point the torque-limiter disengages and one of the first and second torque-limiting interfaces move over the other as opposed to with each other. When rotating a torque limiting assembly within a plastic body with an attachment at the circumferential rim the plastic body will tend to melt if sufficient frictional forces are applied.

Figure 2:
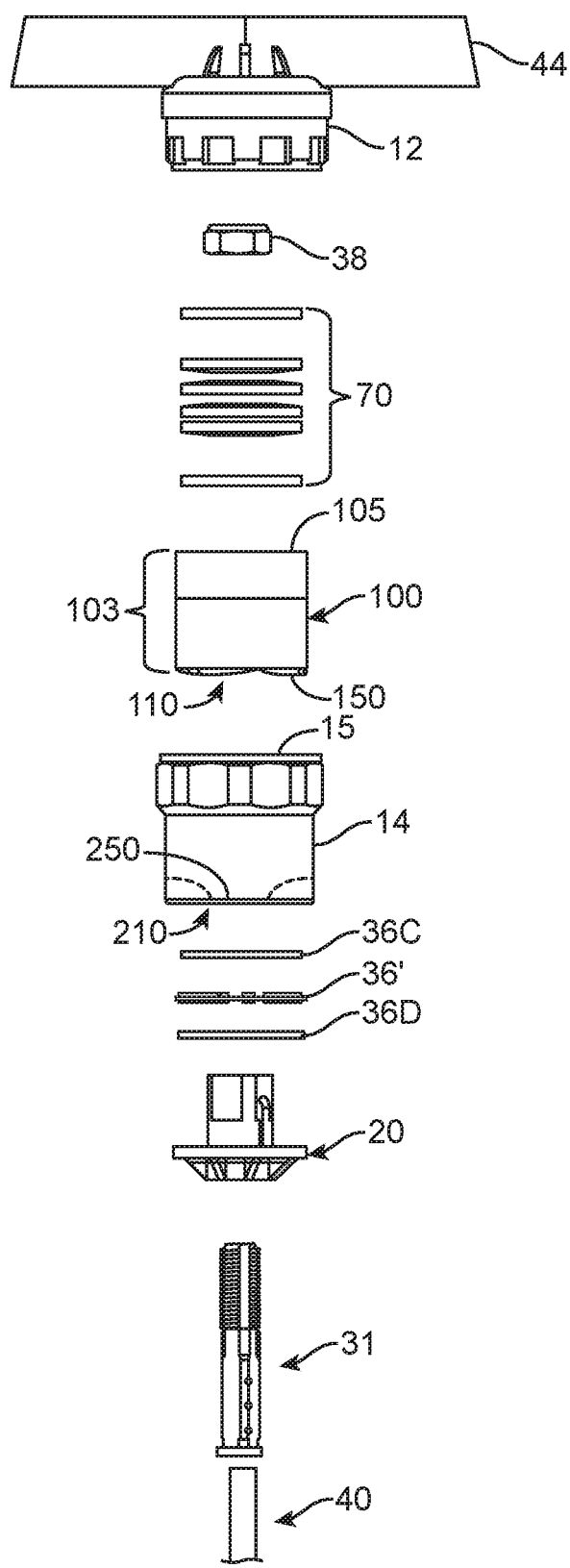
FIG. 2 shows an exploded assembly perspective view back to front of some aspects of a torque limiting device of the present disclosure.

In FIG. 2, aspects and variations of assembly of a torque-limiting device are shown. The driver has a generally cylindrical shape with a cup shaped drive cap 12 with connector mount or other structure to facilitate use by a user. For example, the drive cap is affixed to a generally hollow cylindrical body 14. The cap 12 is mated to the cylindrical body at the proximal end 15 of the cylindrical body. The cap 12 may be snap-fitted to cylindrical body 14, or may be welded, adhered, or attached by any equivalent thereof.

The hollow cylindrical body 14 has an open distal end 16 with a circumferential rim 17 on the exterior therein proving a seat and guide for a tool collar 20. A lower shank 100 is fit inside the body 14. Opposite the circumferential rim on the interior 18 of the cylindrical body 14 is an upper shank component 200 formed as part of the cylindrical hollow body 14 with at least an axial bore 210 and a torque-limiting interface 250 disposed on the inside of the cylindrical body 14.

The tool collar is a guide for a shaft. The tool collar has a flange 22 extending radially of a size and shape to fit rotatably into the circumferential rim 17. The tool collar has a roughly square leg 25 extending on one side of the flange 22 and a nose 27 extending on the opposite of the flange. A shaped channel 29 passes through the tool collar thereby forming a fluid connection.

During assembly the lower shank component 100 fits movably within the hollow body 14. The lower shank has a drive shaft 110 therethrough. On one side of the lower shank lower torque-limiting interface 150 and the other side of the lower shank 100 is a retaining cavity 103 which provides a volume to hold the MBWA 70 configured to position biasing elements, such as a MBWA 70. A tool shaft 32 fits firmly into the tool collar channel 29. The tool shaft may be partially hollow. One or more catches 33 are formed on a portion of the tool shaft whereby the catches mate with the channel 29 and the tool shaft 32 is restricted from rotation within the channel 29. The catches are depicted as one or more flat sides in FIGS. 1A-1C. A tool channel 34 extends axially, at least partially, in the tool shaft. A series of threads 35 are formed on a portion of the tool shaft 32. A first washer 36C, a second washer 36D, and a flat roller bearing washer '36 is interposed between the flange and circumferential rim 17.

The lower shank 100 is once inserted into the body 14 through the proximal end 15 and the lower torque-limiting interface 150 sits on the upper torque-limiting interface 250. The square leg and tool shaft extends through the axial bore 210 and the drive shaft 110. Formed as part of the drive shaft 110 are a series of drive catches 115 which mate with the square legs 25 whereby when the lower shank 100 rotates the square leg rotates as does any tools 40 affixed therein.

The threaded 37 retaining member 38 such as a nut or other fixture fits onto the threads 35 of the tool shaft and is used to compress the MBWA 70 against the lower shank and hold the components inside the device inline. This engagement provides a locking mechanism for tool shaft 32 relative to the body 14 via lower shank 100 when pressure is applied across lower shank 100 and upper shank 200. A preselected force is applied across lower shank 100 and upper shank 200 via MBWA 70 within cylindrical body 14. To seal the device, the drive cap is mounted thereon. At the end of the drive cap 12 is formed a handle 44 for manual use. The MBWA in the manual device preferably provides a force of between about 5 N-m and about 13 N-m.

Figure 3:
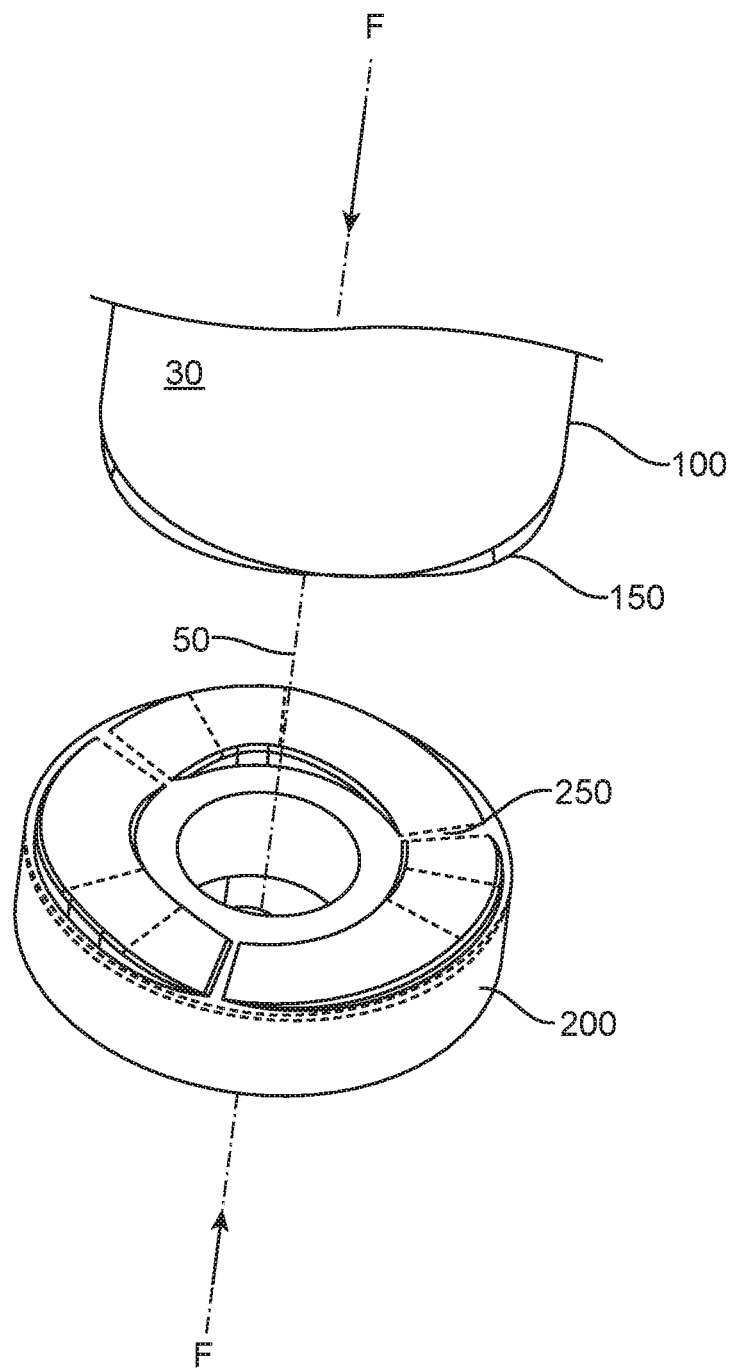
FIG. 3 shows an exploded assembly perspective view of some aspects of torque-limiting mechanisms of the present disclosure.
Figure 4:
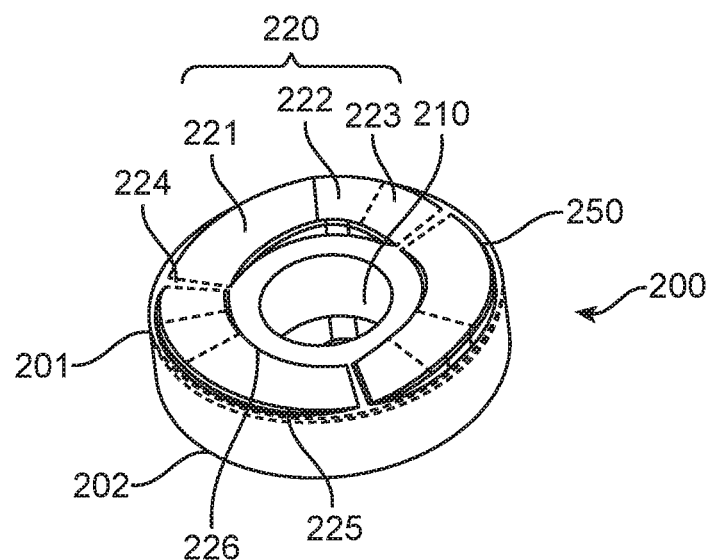
FIG. 4 shows a perspective view of some aspects of the upper shank of the present disclosure.
Figure 5:
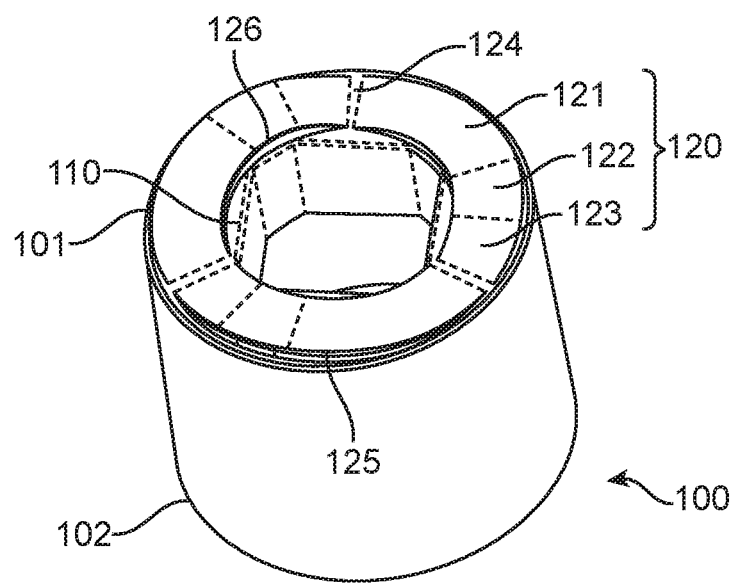
FIG. 5 shows a perspective view of some aspects of components of torque-limiting mechanisms of the present disclosure.

FIGS. 3, 4, and 5 show some additional details and aspects of some implementations of torque-limiting mechanisms of the present disclosure. The torque-limiting mechanisms have the upper shank component 200, the lower shank component 100, and a biasing coil spring configured to apply a force (F) along an axis 50. Upper shank component 200 can have a proximal end 201, a distal end 202, an axial bore 210 connecting the proximal end and the distal end, and a torque-limiting interface 250 disposed on the proximal end. Lower shank component 100 can have a proximal end 101, a distal end 102, a drive socket 110 connecting the proximal end and the distal end, and a torque-limiting interface 150 disposed on the proximal end. The upper shank component and the lower shank component are aligned along an axis 50 in the direction of the axial bore 210 and the drive socket 110 with the torque-limiting interface 250 in contact with the torque-limiting interface 150. The biasing element is configured to apply a compressive force (F) along the axis to compress the torque-limiting interface against the torque-limiting interface. The upper shank component 200 and the lower shank component 100 are configured to engage to generally nest with each other and rotate together when torque is applied to the lower shank component via the drive socket and are configured to disengage when a predetermined torque limit is exceeded. When disengaged, the torque-limiting interfaces 150/250 slide past each other in relative rotation about the axis 50. Drive socket 110 can have any suitable shape that allows for the transmission of torque to the lower shank component 100. Suitable shapes for the drive socket 110 include geometric shape profiles such as hexagons, squares, or truncated/rounded versions thereof.

Those of ordinary skill in the art can appreciate that the torque-limiting mechanisms of the present disclosure can be incorporated into any systems or devices that require torque-limited rotation between subcomponents of those systems or devices. In some implementations, the torque-limiting mechanisms of the present disclosure can be incorporated into torque-limited drivers for use in surgical applications; such drivers can be hand-driven or driven with power tools at higher rates of rotation.

FIGS. 4A-4G and 5 show further aspects of some implementations. Upper shank component 200 can have a torque-limiting interface 250 with a plurality of undulations 220 arranged around the axial bore and separated by a plurality of transition regions 224. The lower shank component 100 can have a torque-limiting interface 150 having a plurality of undulations 120 arranged around the drive socket and separated by a plurality of transition regions 124, the first and second pluralities being equal in number. Each undulation 120/220 can be formed as an upslope 121/221, a peak 122/222, and a downslope 123/223.

The undulations 220 are not gears and are complex shaped waves to balance maintaining nominal torque over a specific number of actuations and limit degradation of inexpensive plastic materials which form the undulations. Such materials will degrade, overheat and/or melt and fail more quickly if subjected to unnecessary friction caused by contact at the torque-limiting interface 150. By shaping specific portions of an undulation 220 as shown in sections A-A through E-E (see FIGS. 6B-6F) the balance of sufficient performance at nominal torque versus degradation is accomplished. Section A-A (FIG. 6C) has a higher shoulder near the center (axial bore 210) of the shank and a slope downward 402 to the perimeter of the shank. Contact between the upper and lower shanks at this section is minimized. This contact area is not the maximum torque transfer area. Section B-B is a region of greater compressive force and by spreading the higher load across a wider plateau 404 the stress on the plastic shanks is distributed in this higher compressive force region. Section C-C provides the widest plateau 406 to further distribute the compressive forces which increase as the lower shank 100 moves around the upper shank 200 along the direction of arrow 1000. Section D-D is the maximum height "H" plateau 408 of the undulation and it is where the maximum compressive forces are applied between shanks, it is a wide plateau to distribute the load. Section E-E provides a transition region wherein compressive forces are reduced and the area of is reduced via a sloping region 410. Shaped undulations disclosed herein maintain predetermined torque ranges without adding excessive wear and heat to the assembly.

In some implementations, the torque-limiting interfaces 150/250 do not contain any step or drop-off greater than about 0.005". One or more cutouts or slots (not shown) can be provided in one or more of the upslopes, 121/221, peaks 122/222, or downslopes 123/223 to collect at least a portion of any debris generated during operation. In some embodiments, downslope 123/223 is designed with maximum length to provide the softest downward angle back down to the initial height of the next upslope 121/221. During powered rotation, a softer downslope mitigates degradation of the downslope 123/223 material. Such degradation adversely impact performance as the torque-limit at which disengagement occurs can change as the material degrades.

Each undulation 120/220 sweeps through a portion of the 360 degrees around the central axial bore 210 or drive socket 11, with the plurality of undulations 120/220 covering a total portion of the 360 degrees around the central axial bore. In some implementations, the total portion covered by the plurality of undulations 120/220 can be at least about 65% of the 360 degrees (about 235 degrees), at least about 70% of the 360 degrees (about 255 degrees), at least about 80% of the 360 degrees (about 285 degrees), at least about 83% of the 360 degrees (about 300 degrees), at least about 90% of the 360 degrees (about 324 degrees), at least about 95% of the 360 degrees (about 345 degrees), or at least about 98% of the 360 degrees (about 350 degrees). The portion not covered by the plurality of undulations 120/220 is filled with transition regions 124/224 between the end of each downslope 123/223 and the beginning of the next upslope 121/221. Each transition region 124/224 can be selected to be no greater than about 35 degrees, no greater than about 20 degrees, no greater than about 15 degrees, no greater than about 10 degrees, no greater than about 5 degrees, no greater than about 4 degrees, no greater than about 3 degrees, no greater than about 2 degrees, no greater than about 1 degree, or can be eliminated entirely if the end of each downslope 123/223 is immediately adjacent to the beginning of the next upslope 121/221.

A softer downslope angle the torque-limiting interfaces 150/250 can substantially mitigate or eliminate any "click" or audible indication that the upper shank component 200 and lower shank component 100 have slipped past each other during a disengagement, also referred to herein as an actuation, when the predetermined torque limit has been exceeded. In some implementations, an actuation indicating system can be incorporated in the overall torque-limiting driver to create one or more "clicks" when the upper shank component 200 and lower shank component 100 have slipped past each other. In some implementations, the actuation indicating system can include a flag feature on either lower shank component 100 or upper shank component 200 that impacts one or more spokes, protrusions, or other physical features on another component in the system as relative rotation occurs.

Upper shank component 200 and lower shank component 100 can be formed from various materials. Suitable materials include stainless steels, aluminums, plastic materials, or composites including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. In some implementations, 30% glass-filled polyetherimide can be used to form one or more of the above components. For components formed from stainless steels or aluminums, the shank components can be heat treated, passivated, or anodized via suitable methods known to those of ordinary skill in the art. In some implementations, aluminum shank components can be finished with a hard anodize finish per MIL-A-8625F, type III, class 2. In some implementations, stainless steel 440c shank components can be heat treated per AMS 2759/5D to 58Rc and passivated with treatment with nitric acid and/or sodium dichromate. Other heat treatments and passivation methods known in the art are also suitable. In some implementations, corresponding pairs of gear rings are formed from different materials. In some preferred implementations, one shank component 100/200 is formed from stainless steel or aluminum and the corresponding gear ring is formed from 30% glass-filled polyetherimide (PEI) resin. In some implementations the shank components 100/200 can be made from the same material.

According to aspects of one or more exemplary implementations, components of the torque-limiting mechanisms of the present disclosure are resistant to sterilization, cleaning, and preparation operations. For example, the upper shank component and lower shank component may be configured to withstand sterilization by methods including radiation (e.g., gamma rays, electron beam processing), steam (e.g., autoclave), detergents, chemical (e.g., Ethylene Oxide), heat, pressure, inter alia. For example, materials may be selected according to resistance to one or more selected sterilization techniques.

The material selection and surface treatments applied to the torque-limiting interfaces 150/250 can affect the predetermined torque limit. The static friction between the torque-limiting interfaces 150/250 determines when disengagement will occur, as the rotation force can overcome the static friction holding the interfaces into engagement with each other. Greater contact surface area of the opposing interfaces, via wider undulations 120/220 or other aspects of the shape/profile of the undulations 120/220, will increase the resistance to actuation and lead to a higher predetermined torque limit.

In some preferred implementations, upper shank component 200 and lower shank component 200 are both mad from 30% glass-filled polyetherimide (PEI) resin. In some implementations, a glass-filled ULTEM® PEI from Saudi Basic Industries Corporation (SABIC) can be used to form the upper shank component 200 and lower shank component 200 via machining or molding. In some implementations, a lubricant is disposed on one or both of torque-limiting interfaces 150/250. Such lubricants are useful to avoid excessive heat build-up during actuations at high rates of rotation, which can melt or degrade the PEI material.

Figure 6A:
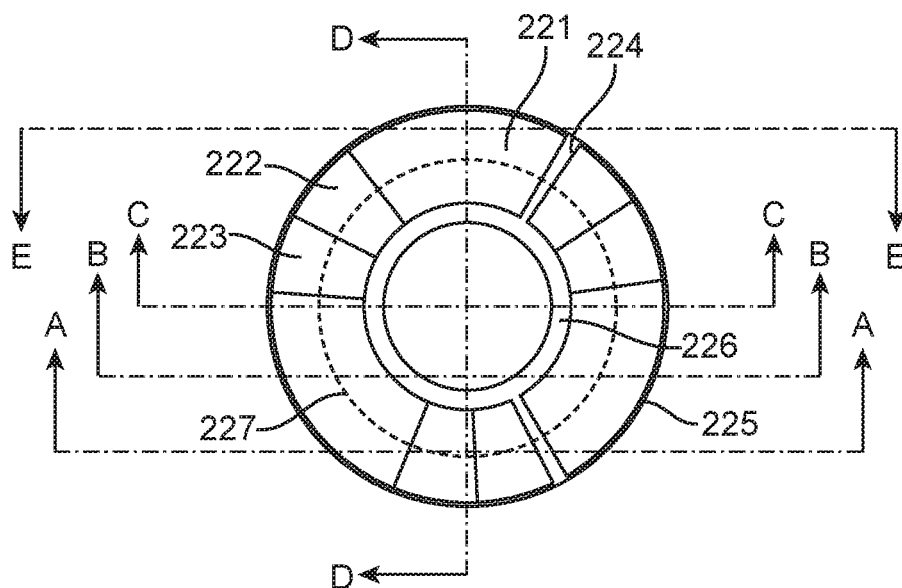
FIG. 6A shows a top view of some aspects of components of torque-limiting mechanisms of the present disclosure.
Figure 6B:
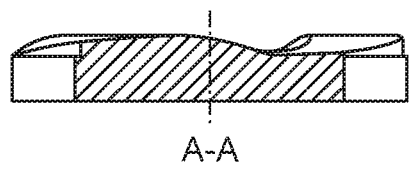
FIGS. 6B-6F show cut-away sectional views along the sections marked A-A, B-B, C-C, D-D, and E-E in FIG. 4A.
Figure 6E:
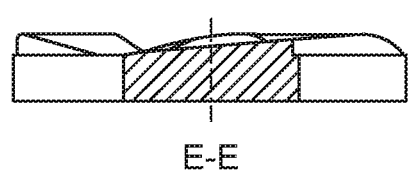
Figure 6C:
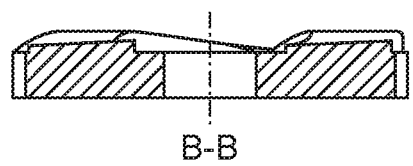
Figure 6F:
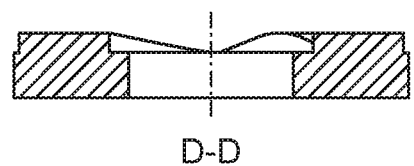
Figure 6D:
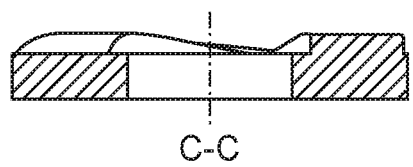

The shape of some implementations of undulations 120/220 can be seen in FIGS. 6A-6F. FIG. 6A shows a top view of the torque-limiting interface 150 at the proximal end 201 of upper shank component 200. FIG. 6B shows a cut-away view of the upper shank component 200 along line A-A shown in FIG. 6A. FIG. 6C shows a cut-away view of the upper shank component 200 along line B-B shown in FIG. 6A. FIG. 6D shows a cut-away view of the upper shank component 200 along line C-C shown in FIG. 6A. FIG. 6E shows a cut-away view of the upper shank component 200 along line E-E shown in FIG. 6A. FIG. 6F shows a cut-away view of the upper shank component 200 along line D-D shown in FIG. 6A. The number of undulations 120/220 is determined by the size of the upper shank component 200 and lower shank component 100 and the shape of the undulations 120/220. The size of the shank components 100/200 determines the functional path length that the plurality of undulations may have. The functional path length refers to the circumferential length of a circular path along the midpoint of the undulations, shown as a dashed circle 227 in FIG. 6A. A larger diameter shank component allows for a larger functional path length. The shape of the undulations 120/220 refers to the inclination angle of the upslope 121/221, the length of the peak 122/222, and the declination angle of the downslope 123/223. Sharper inclination and declination angles and shorter peak lengths can lead to a shorter functional path length for each individual undulation, which would allow for more undulations to be placed onto the torque-limiting interfaces 150/250. The torque-limiting interfaces may have two undulations, three undulations, four undulations, or five or more undulations. Three or more undulations are used in some preferred implementations, as systems with only two undulations may be less stable during actuations at higher rates of rotation.

The width of the undulations can span the entirety of the annular ring of the proximal ends of the upper shank component and lower shank component between the drive socket 110 or axial bore 210 and outer edges of those components, or can be reduced widths to accommodate adjoining parts to avoid undesired contact points or friction. The width must be sufficient to provide adequate interface contact area with the opposing set of waves to create the friction necessary for torque transmission. Larger widths allow for the applied force to be distributed over larger surface areas and reduce stress on the components.

The inclination angle of each upslope 121/221 can be about 3 to about 15 degrees, more preferably about 5 to about 9 degrees, more preferably about 6 to about 8 degrees, and most preferably about 7 degrees. The inclination angle is measured along the functional path length along the midpoint of the undulations, as the angle along the interior edge 126/226 will be higher due to the shorter path length, and the angle along the exterior edge 125/225 will be lower due to the longer path length. The declination angle of each downslope 123/223 can be about 5 to about 45 degrees, more preferably about 10 to about 30 degrees, more preferably about 10 to about 20 degrees, and most preferably about 15 degrees. The declination angle is measured along the functional path length along the midpoint of the undulations. In some preferred implementations, the ratio of the functional path length of the upslope 121/221 of each undulation to the functional path length of the downslope of each undulation can be about 3.0:1, about 2.5:1, about 2.4:1, about 2.3:1, about 2.2:1, about 2.1:1, about 2.0:1, about 1.9:1, about 1.8:1, about 1.7:1, about 1.6:1, about 1.5:1, about 1.4:1, about 1.3:1, about 1.2:1, about 1.1:1, or about 1.0:1. In some preferred implementations the ratio can be between about 2.2:1 and about 1.8:1, or more preferably about 2.0:1.

Each peak 122/222 has an even height across its surface from the interior edge 126/226 to the exterior edge 125/225 at each radial line from the central axis of the respective shank component 100/200. In some implementations the functional path length of each peak 122/222 is approximately equal to the length of each of the transition regions 124/224, such that the peaks 122/222 of each torque-limiting interface are complementary and mate with the transition regions 124/224 of the opposing torque-limiting interface.

FIGS. 7A-7D show some aspects of an implementation of a lower shank component 100 the present disclosure. FIG. 7A and FIG. 7B show perspective views of an implementation of a lower shank component 100. FIG. 7C shows a side view while FIG. 7D shows a cross-sectional view along the line D-D shown in FIG. 7C. The lower shank component 100 can include a retaining cavity 103 configured to retain biasing element within an annular wall 104 located at the distal end 102. The retaining cavity 103 provides for a volume in which a biasing element 300 can be compressed, so that if biasing element 300 expands radially during compression it will be retained within retaining cavity 103 rather than impinging or contacting other components within the system.

Biasing element 30 provides compressive force between the upper shank component and lower shank component to place the torque-limiting interfaces 150/250 into frictional contact with each other. Suitable biasing elements can include springs, spring washers, also referred to as Belleville washers, grommets or washers of compressible materials such as rubber. In some implementations, compressible materials with durometer ratings between about 50 durometer and 100 durometer can be used as biasing elements. The biasing element can be compressed by other components in a torque-limiting driver. The amount of compression applied to a biasing element can be used to set the predetermined torque limit at which disengagement/actuation of the torque-limiting mechanism occurs. Higher compressive forces created by the biasing element will create higher predetermined torque limits.

According to aspects of one or more exemplary implementations, the torque-limiting mechanisms of the present disclosure are capable of imparting torques of up to about 6 N-m at various rotational speeds. For example, the torque output range may be selected between about 0.5 N-m and about 6 N-m and utilized in combination with a rotational speed selected between about 150 RPMs and about 1300 RPMs. Typically, the torque requirement is different for different operations and for different implants. For example, applications may include those in the field of orthopedic surgery, construction and emplacement of implants, etc. In such instances, the predetermined torque limit may be about 6 N-m, depending on an implant's specifications. Smaller fasteners may utilize lower torque limits between about 0.1 N-m and about 2.0 N-m. In some instances the torque-limiting mechanisms of the present disclosure will provide a predetermined torque of at least one of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 Newton-meters (N-m) of torque at a rotational speed of at least one of 50, 100, 150, 200, 250, 300, 350, 400, 450, 500, 550, 600, 650, 700, 750, 800, 850, 900, 950, 1000, 1050, 1100, 1150, 1200, 1250, or 1300 RPMs over at least one of 5, 10, 20, 30, 40, 50, 60, 70, 80, 90, 100, 105, 110, 120, 150, 180, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 actuations while remaining within a specified operational range.

FIGS. 6A and 6B show testing data of an implantation of a torque-limiting mechanism of the present disclosure. A torque-limiting driver that incorporated a torque-limiting mechanism having the torque-limiting interfaces shown in FIGS. 2, 3, and 6A-6F formed from 30% glass-filled PEI resin was assembled and tested at 450 RPM with a predetermined torque limit of about 1.05 N-m. The torque-limiting driver was rotated at 450 RPM for 1 second intervals and the torque output was measured with an electronic torque transducer. FIG. 8A shows that the torque limit remained within an operational range of about 0.9 to about 1.1 N-m over approximately 2,200 actuations. FIG. 8B shows data for two 1-second intervals and shows the actuations that occur over those 1-second intervals. Approximately 22 actuations, from 7.5 revolutions per second at 450 RPM, occur in each 1-second interval, with the applied torque remaining within the operational range.

FIGS. 8C and 8D show the torque output profiles of torque-limiting drivers over a single hand-driven actuation. FIG. 8C shows the torque profile of a traditional crown gear interface with opposing sets of jagged teeth, such as that disclosed in U.S. Pat. No. 7,938,046, incorporated herein in its entirety for all purposes. The resulting profile shows a spike drop-off in torque as the opposing teeth slip off each other sharply. Systems incorporating these jagged teeth crown gears exhibit inconsistent torque-limits across ranges of rotational speeds, with higher rotational speeds showing higher torque. In contrast, FIG. 6D shows a torque output profile from the system used in FIGS. 6A and 6B, which incorporates the three-undulation torque-limiting interfaces shown in FIGS. 2, 3, 4A-4F and described more fully elsewhere herein. The torque output increases and decreases more gradually and smoothly through each actuation, which provides for a more consistent torque-limit across rotational speeds, including higher rotational speeds up to 1300 RPM. Further, the torque-limiting mechanisms are more durable and can last through a higher number of actuations, including over 2,000 actuations, while remaining within a specified operational range.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A disposable torque limiting device comprising:
a generally hollow cylindrical body with a partially closed distal end;
an upper shank formed inside the partially closed distal end of the cylindrical body; a circumferential rim formed on the inside of the partially closed dial end;
an upper torque-limiting interface formed on the inside of the partially closed distal end having a axial bore;
a lower shank component comprising a proximal end, a distal end, a drive shaft extending from the distal end a drive socket connecting the proximal end and the distal end, and a lower torque-limiting interface disposed on the proximal end;
wherein the lower shank component is rotatable within the cylindrical body and the upper shank component and the lower shank component are aligned along an axis in the direction of the axial bore, the lower shank component is rotatable with in the cylindrical body and the drive socket with the first torque-limiting interface in contact with the second torque-limiting interface;
a Multiple Belleville Washer Assembly "MBWA" is placed above the lower shank on at least partially around a tool shaft configured to apply compressive force along the axis to compress the first torque-limiting interface against the second torque-limiting interface;
a tool collar with a flange extending radially, a front on one side of the flange, a square leg formed on the opposite of the flange and a shaped channel there through rotatably fit into the circumferential rim;
the tool shaft has a threaded back portion and a front end having a tool channel therein;
catches formed on the tool shaft configured to mate with the shaped channel whereby the tool shaft can be inserted through the tool collar and restrict rotation within the shaped channel;
a threaded retaining member configure to engage the threaded back portion;
wherein the tool shaft and threaded retaining member cooperate to apply a predetermined force to the lower and upper shanks via affixation of the tool shaft through the tool collar, the axial bore, the drive socket and the MBWA and affixing the retaining member thereto.

2. The device of claim 1 wherein:
the MBWA configured to apply compressive force along the axis to compress the first torque-limiting interface against the second torque-limiting interface;
the upper shank component and the lower shank component are configured to engage to rotate together when torque is applied to the lower shank component via the drive socket; and,
the upper shank component and the lower shank component are configured to disengage when a predetermined torque limit is exceeded.

3. The device of claim 1 further comprising a plastic high lubricity washer between the flange and the circumferential rim.

4. The device of claim 1 further comprising a roller bearing washer between the flange and the circumferential rim.

5. The device of claim 1 further comprising a tool in the tool channel.

6. The device of claim 1 wherein the MBWA is configured to have at least one grouping of three stacked cone to a base members the MBWA.

7. The device of claim 6 wherein the first torque-limiting interface and second torque-limiting interface each comprise three undulations.

8. The device of claim 7 wherein each undulation is a complex shaped wave which limits degradation of inexpensive plastic materials and provides nominal torque.

9. The device of claim 7 further comprising:
a first section of each undulation with a higher peak near the interior edge of the shank and a downslope to the perimeter of the upper shank; and,
a second section having a wide upslope.

10. The device of claim 1 wherein the MBWA is configured to have at least three stacked cones facing cone to cone at least three one cone members positioned between two flat washers.

11. A disposable torque limiting device comprising:
a generally hollow cylindrical body with a partially closed distal end;

an upper shank formed inside the partially closed distal end of the cylindrical body; a circumferential rim formed on the inside of the partially closed dial end;

an upper torque-limiting interface having undulations formed on the inside of the partially closed distal end having an axial bore;

a lower shank component rotatable placed within the cylindrical body comprising a proximal end, a distal end, a retaining cavity formed therein, a drive socket fluidly connecting the proximal end and the distal end, and a lower torque-limiting interface having undulations disposed on the proximal end, wherein the upper shank component and the lower shank component are aligned along an axis in the direction of the axial bore and the drive socket with the first torque-limiting interface in contact with the second torque-limiting interface;

an MBWA placed within the retaining cavity configured to apply compressive force along the axis to compress the first torque-limiting interface against the second torque-limiting interface at a predetermined torque limit;

a tool collar with a flange extending radially, a front on one side of the flange, a square leg formed on the opposite of the flange and a shaped channel there through rotatably fit into the circumferential rim;

a tool shaft with a threaded back portion and a front end having a tool channel therein;

catches formed on the tool shaft configured to mate with the shaped channel whereby the tool shaft can be inserted through the tool collar but restrict rotation within the shaped channel; and, a threaded retaining member configure to engage the threaded back portion.

12. The device of claim 11 wherein each undulation is a complex shaped wave which limits degradation of inexpensive plastic materials and provides nominal torque.

13. The device of claim 12 further comprising:

a first section of each undulation with a higher peak near the interior edge of the shank and a downslope to the perimeter of the upper shank; and, a second section having a wide upslope.

14. The device of claim 13 wherein:

the MBWA is configured to apply compressive force along the axis to compress the first torque-limiting interface against the second torque-limiting interface;

the upper shank component and the lower shank component are configured to engage to rotate together when torque is applied to the lower shank component via the drive socket; and, the upper shank component and the lower shank component are configured to disengage when a predetermined torque limit is exceeded.

15. The torque-limiting device of claim 13 further comprising a power unit attached to the drive shaft.

16. The torque-limiting device of claim 13 wherein the torque-limiting mechanism provides a predetermined torque between about 0.1 Newton-meters and about 6 Newton-meters of torque at a rotational speed between about 50 RPM and about 1300 RPM over at least one of 5, 10, 20, 30, 40, 50, 60, 70, 80, 90, 100, 110, 120, 150, 180, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, or 2500 actuations while remaining within a specified operational range.

17. The device of claim 11 further comprising a roller bearing washer between the flange and the circumferential rim.

18. The torque-limiting device of claim 11 wherein:

the undulations of the first torque-limiting interface are arranged around the axial bore and separated by a first plurality of transition regions;

the undulations of the second torque-limiting interface are arranged around the drive socket and separated by a second plurality of transition regions, the first and second pluralities being equal in number; and each undulation comprises an upslope, a peak, and a downslope.

19. The torque-limiting device of claim 18 wherein each upslope has an inclination angle between about 3 degrees and about 15 degrees.

20. The torque-limiting device of claim 18 wherein each upslope has an inclination angle between about 5 degrees and about 9 degrees.

21. The torque-limiting device of claim 18 wherein the predetermined torque limit is between about 0.1 Newton-meters and 3.0 Newton-meters.

22. The torque-limiting device of claim 18 wherein the predetermined torque limit is between about 3.0 Newton-meters and 6.0 Newton-meters.

23. The torque-limiting device of claim 18 wherein the first torque-limiting interface and second torque-limiting interface each comprise between two and five undulations.

* * * * *